United States Patent [19]

Solomon et al.

[11] 4,361,504

[45] Nov. 30, 1982

[54] PROCESS FOR MAKING A SILVER CATALYST USEFUL IN ETHYLENE OXIDE PRODUCTION

[75] Inventors: Jeffry A. Solomon; Harold W. Young, Jr., both of Baton Rouge, La.

[73] Assignee: The Dow Chemical Company, Midland, Mich.

[21] Appl. No.: 299,363

[22] Filed: Sep. 4, 1981

[51] Int. Cl.³ .................. B01J 21/04; B01J 23/50
[52] U.S. Cl. .................................... 252/463; 252/476
[58] Field of Search ............................. 252/463, 476

[56] References Cited

U.S. PATENT DOCUMENTS

| | | | |
|---|---|---|---|
| 2,920,052 | 1/1960 | Martin | 252/476 X |
| 3,563,914 | 2/1971 | Wattimena | 252/463 |
| 4,007,135 | 2/1977 | Hayden et al. | 252/476 X |
| 4,226,782 | 10/1980 | Hayden et al. | 252/476 X |

*Primary Examiner*—W. J. Shine
*Attorney, Agent, or Firm*—A. C. Ancona

[57] ABSTRACT

An improved process of making a silver catalyst which comprises impregnating a suitable support with an aqueous ammoniacal solution of a silver salt of an organic carboxylic acid and reducing said salt in the presence of a polyhydroxy compound.

8 Claims, No Drawings

PROCESS FOR MAKING A SILVER CATALYST USEFUL IN ETHYLENE OXIDE PRODUCTION

BACKGROUND OF THE INVENTION

Silver catalysts are well known in the art as useful in the production of ethylene oxide by the vapor phase oxidation of ethylene with molecular oxygen at elevated temperature. Much is taught in the literature concerning preparation of such catalysts and a variety of methods have been suggested which produce small particles of silver and relatively uniform distribution on a suitable support.

Generally, the support is impregnated or coated with a solution of the salt of the metal or metals to be employed. This is followed by drying and a subsequent reduction. Although the reducing step can be a thermal reduction in the presence of air or an inert gas (U.S. Pat. No. 2,709,123), hydrogen and hydrazine (U.S. Pat. No. 3,575,888) have also been employed for the reduction. Reducing agents in the form of organic compounds have been added to the catalyst, either by simultaneous application or subsequent addition to the catalytic component. Also reducing compounds have been known to be employed by incorporating them into the support prior to the addition of the catalytic component.

In one early patent (U.S. Pat. No. 2,920,052) a silver salt of an organic acid, e.g. silver oxalate, was used for the silver source and the reduction was carried out by wetting with diethylene glycol and heating to reduce the silver salt and to remove the excess glycol. The use of silver salts of carboxylic acids was also taught in an earlier patent (U.S. Pat. No. 2,446,132) and glycols were suggested as reducing agents (U.S. Pat. No. 3,563,914). In one procedure (U.S. Pat. No. 3,702,259) silver carboxylates are employed with an "organic amine solubilizing/reducing" agent or ammonia may be used with the organic amine. In another similar procedure the impregnation is followed by a methanol wash prior to reduction (U.S. Pat. No. 4,102,820).

Other nitrogen-containing compounds, e.g. polyacrylonitrile (U.S. Pat. No. 3,892,679), an alkanolamine or an acid amide (U.S. Pat. No. 4,248,740) have also been employed. While the solvent used to apply the reducing agent is frequently water as in U.S. Pat. No. 3,702,259 above, organic solvents have also been employed, as for example, ethylene carbonate, dimethyl formamide and dimethyl sulfoxide as solvents for the polyacrylonitrile in U.S. Pat. No. 3,892,679, above.

Supports taught in the art are silica, alumina or other inert low surface area support materials. For example α-alumina is disclosed as a useful support in U.S. Pat. Nos. 3,305,492 and 3,172,893.

Various methods are used for incorporating the silver salt and include vacuum-impregnation (U.S. Pat. No. 3,702,259) which apparently provides a more complete coverage of the support surfaces.

The present invention is a new combination of old steps in which the silver salt of an organic acid, e.g. silver acetate, is dissolved in aqueous ammonium hydroxide. This solution is used to impregnate the support. The impregnated support is dried at low temperature, and then contacted with a polyhydroxy compound, e.g. monoethylene glycol, and reacted therewith to reduce the silver salt. This is followed by a water-wash and a final drying at low temperature (about 50° to about 150° C.).

SUMMARY OF THE INVENTION

A silver catalyst having small sized silver crystallites is prepared by impregnating a porous alumina support with a solution of a silver salt of an organic carboxylic acid in aqueous ammonium hydroxide. The impregnated support is dried at low temperature, then contacted with a polyhydroxy compound for a time sufficient to reduce substantially all the silver salt to the metal. The reduced catalyst is then washed with water and dried at a low temperature prior to use.

DETAILED DESCRIPTION OF THE INVENTION

The present invention employs supports known to the art which have relatively small surface areas and are inert, alumina being preferred. The surface area should generally be less than 2 m$^2$/g. A particular alumina known as α-alumina is a most useful support material.

The useful silver salts of organic acids include both aliphatic mono- and di-carboxylic acids. Thus, for example, the silver salts of formic, acetic, propionic, oxalic, malonic, succinic as well as others of each series are useful as sources of silver. Other acids include the simple aromatic acids such as benzoic, toluic and phenyl acetic acids.

The silver salt is always applied to the support from aqueous ammoniacal solution. Dispersing agents such as gum arabic and promoters such as sodium, potassium, cesium, tin, gold, barium, calcium, cadmium and the like can also be added to the solution used to impregnate the silver salt onto the support.

The reducing agents useful in converting the silver salts to silver include glycols, e.g. mono-, di- and triethylene glycols, and glycerine.

The reduction may be accomplished at room temperature, but heat may be applied to shorten the reaction time. Temperatures of from about 20° to about 200° C. may be employed, preferably about 140° to about 180° C.

The following examples of the invention together with comparative examples illustrate the advantages of the present invention.

EXAMPLE 1

Twenty-one grams of silver acetate and 0.5 gm of barium acetate were dissolved in 24 cc of concentrated ammonium hydroxide and added to 16 gm of 30% (wt) aqueous gum arabic solution. The resulting solution was vacuum-impregnated onto 100 gm of α-alumina support, and vacuum-dried at 60°–75° C. for one-half hour. This dried material was then dropped into 160° C. monoethylene glycol and heated for one-half hour, to reduce the silver salt. The catalyst was removed from this glycol mixture, washed overnight with water in a Soxhlet extractor, and then dried at 90° C. for 4 hours.

This treatment resulted in a catalyst containing 7% silver (w/w) and having an average crystallite size of 218 Å. The catalyst was loaded into a quarter-inch by 14-inch tube heated by circulating oil. The catalyst was then treated with a gas consisting of 6% oxygen, 5% ethylene, 7% carbon dioxide, and the remainder nitrogen. After a conditioning period, a 30% conversion was achieved at 250° C. with a 74% selectivity to ethylene oxide.

The following catalyst was made substantially according to the procedure of U.S. Pat. No. 3,887,491.

COMPARATIVE EXAMPLE A

Forty-five grams of silver nitrate and 0.3 gm of barium nitrate were dissolved in 24 cc of distilled water, and mixed with 16 gm of 30% gum arabic solution. The resulting solution was vacuum-impregnated onto 100 gm of α-alumina support, and vacuum-dried at 70° C. for one-half hour. This dried material was then dropped into 250° C. mineral oil, and heated one-half hour to reduce the silver salt. When removed from this oil bath, the catalyst was heated in air at 300° C. for one-half hour to remove the oil.

The foregoing treatment resulted in a catalyst containing 20% silver, having an average crystallite size of 366 Å. This catalyst was loaded into a quarter-inch by 14-inch tube heated by circulating oil. A feed gas consisting of 6% oxygen, 5% ethylene, 7% carbon dioxide, and the remainder nitrogen was passed over the catalyst. After a preliminary conditioning period, a 30% conversion was achieved at 270° C. with a 70% selectivity to ethylene oxide.

EXAMPLE 2

Silver acetate (1710 gm) and barium nitrate (11 gm) were dissolved in 5400 cc of concentrated ammonium hydroxide and added to 720 gm of 30% aqueous gum arabic solution. The resulting solution was vacuum-impregnated onto 4500 gm of α-alumina spherical support, and vacuum-dried at 70° C. for one hour. The dried impregnated support was then placed in monoethylene glycol at 160° C. for one hour to reduce the silver salt to silver metal. The catalyst was then washed several times with distilled water, and dried 2 hours at 100° C., 2 hours at 120° C., and 40 hours at 140° C.

The catalyst thus prepared contained 6% silver, and had an average crystalline size of 209 Å. The catalyst was loaded into a tube 1½ inches in diameter and 20 feet long, heated by circulating oil. Using a gas stream of 6% oxygen, 5% ethylene, and 7% carbon dioxide in nitrogen, a conversion of 30% was obtained at 260° C. with a 74.2% selectivity to ethylene oxide.

COMPARATIVE EXAMPLE B

Silver nitrate (2025 gm) and barium nitrate, (13.5 gm) dissolved in 1080 cc of distilled water, were added to 720 gm of 30% gum arabic, and then impregnated onto 4500 gm of α-alumina support. This material was dried, reduced, and heated as in Example 2.

The resulting catalyst contained 19.8% silver, with an average crystallite size of 360 Å. Under the same reaction conditions as Example 3, this catalyst achieved a 30% converstion at 288° C., with a 70.4% selectivity to ethylene oxide.

EXAMPLE 3

Silver oxalate (38 gm) and a sufficient quantity of barium oxalate were dissolved in 30 cc of ammonium hydroxide (concd). This solution was then impregnated onto 40 gm of α-alumina support, dried, and reduced as in Example 1. The catalyst was then heated in air for one-half hour at 200° C. to remove any residual glycol.

The resulting catalyst contained 18.8% silver, with an average crystalline size of 290 Å. This catalyst was loaded into the reactor of Example 1, and treated with the gas of Example 1. A 30% conversion was obtained at 250° C., with a 74.5% selectivity to ethylene oxide.

We claim:
1. A process for making a supported silver catalyst which comprises:
   a. impregnating an inert porous support material with an aqueous solution of a silver salt of an organic carboxylic acid containing ammonium hydroxide,
   b. drying said impregnated support material at low temperature,
   c. reducing said silver salt on said impregnated support material by reacting said salt with a polyhydroxy compound to form said catalyst,
   d. removing residual reactants from said catalyst by washing with water, and
   e. drying at low temperature prior to use.
2. The process of claim 1 wherein the support material is an α-alumina.
3. The process of claim 2 wherein the silver salt is the salt of a dicarboxylic acid.
4. The process of claim 3 wherein the dicarboxylic acid is oxalic acid.
5. The process of claim 1 wherein the polyhydroxy compound of step c is a glycol.
6. The process of claim 5 wherein the glycol is monoethylene glycol.
7. The process of claims 5 or 6 wherein the temperature of reduction of step c is from about 140° to about 180° C.
8. The process of claims 4, 5 or 6 wherein the aqueous ammonium hydroxide is concentrated ammonium hydroxide.

* * * * *